United States Patent
Campbell et al.

(10) Patent No.: US 6,475,239 B1
(45) Date of Patent: Nov. 5, 2002

(54) METHOD FOR MAKING POLYMER HEART VALVES WITH LEAFLETS HAVING UNCUT FREE EDGES

(75) Inventors: Louis A. Campbell; Riyad Moe; Edward J. Sarnowski, all of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/170,925

(22) Filed: Oct. 13, 1998

(51) Int. Cl.[7] ............................................... A61F 2/24
(52) U.S. Cl. ........................ 623/2.12; 623/901; 264/299
(58) Field of Search ........................... 623/2, 900, 901, 623/2.12, 2.15, 2.19; 264/299, 320, 328.8

(56) References Cited

U.S. PATENT DOCUMENTS

| | | | |
|---|---|---|---|
| 4,009,648 A | 3/1977 | Braden et al. | 98/40 |
| 4,262,802 A | 4/1981 | Laauwe | 206/540 |
| 4,291,420 A | 9/1981 | Reul | 3/1.5 |
| 4,364,127 A | 12/1982 | Pierce et al. | 3/1.5 |
| 4,416,029 A | 11/1983 | Kaster | 3/1.5 |
| 4,451,936 A | 6/1984 | Carpentier et al. | 3/1.5 |
| 4,473,423 A | 9/1984 | Kolff | 156/245 |
| 4,510,628 A | 4/1985 | Kolff | 3/1.5 |
| 4,759,758 A | 7/1988 | Gabbay | 623/2 |
| 4,778,461 A | 10/1988 | Pietsch et al. | 623/2 |
| 4,888,009 A | 12/1989 | Lederman et al. | 623/2 |
| 5,116,564 A | 5/1992 | Jansen et al. | 264/255 |
| 5,192,313 A | 3/1993 | Budd et al. | 623/2 |
| 5,207,707 A | 5/1993 | Gourley | 623/2 |
| 5,306,295 A | 4/1994 | Kolff et al. | 623/3 |
| 5,376,113 A | 12/1994 | Jansen et al. | 623/2 |
| 5,439,143 A | 8/1995 | Brown et al. | 222/185 |
| 5,500,016 A | 3/1996 | Fisher | 623/2 |
| 5,562,729 A | 10/1996 | Purdy et al. | 623/2 |
| 5,728,976 A | 3/1998 | Santuncci et al. | 174/135 |

FOREIGN PATENT DOCUMENTS

| | | | |
|---|---|---|---|
| EP | 0 224 153 A2 | | 11/1986 |
| FR | 2591100 | * | 6/1987 |
| GB | 1443221 | * | 7/1976 |
| WO | WO 97/41808 | | 11/1997 |

OTHER PUBLICATIONS

Polyurethane Rubber Heart Valves, Finelli et al pp. 892–895.*

Christie, G. W., et al., The Bovine Pericardial Bioprosthetic Heart Valve: Methods for Tensile Stress Reduction in the Leaflets During the Loaded Phase, Advances in Bioengineering, BED–vol. 20, 1991, pp. 647–650.

Leat, M. E., et al., The Influence of Manufacturing Methods on the Function and Performance of a Synthetic Leaflet Heart Valve, Journal of Engineering in Medicine, vol. 209, 1995, pp. 65–69.

Clift, S. E., et al., Finite Element Stress Analysis of a New Design of Synthetic Leaflet Heart Valve, Journal of Engineering in Medicine, 1996, vol. 10, pp. 267–272.

Christie, G. W., et al., Stress–Related Failure Modes of Bovine Pericardial Heart Valves, Surgery for Heart Valve Disease, pp. 765–779.

Christie, G. W., et al., On Stress Reduction in Bioprosthetic Heart Valve Leaflets by the Use of a Flexible Stent, Journal of Cardiac Surgery, vol. 6, No. 4, 1991, pp. 476–481.

Corden, J., et al., The Influence of Open Leaflet Geometry on the Haemodynamic Flow Characteristics of Polyurethane Trileaflet Artificial Heart Valves, Journal of Engineering in Medicine, 1996, vol. 210, pp. 273–287.

(List continued on next page.)

*Primary Examiner*—Bruce Snow
(74) *Attorney, Agent, or Firm*—Blossom E. Loo

(57) ABSTRACT

A method for manufacturing a prosthetic heart valve. An elastic valve body and at least one leaflet are formed on a mold. The leaflet has a free edge which is formed by the mold without cutting the leaflet at the free edge.

12 Claims, 7 Drawing Sheets

OTHER PUBLICATIONS

Mackay, T. G., et al., In Vitro Function and Durability Assessment of a Novel Polyurethane Heart Valve Prosthesis, Artificial Organs, 20(9), 1017–1025.

Hulsbergen, M. H., et al., Elastomeric Valves, A New Design, The International Journal of Artificial Organs, vol. 18, No. 4, 1995, pp. 203–209.

Jansen, J., et al., A Synthetic Three–Leaflet Valve, Journal of Medical Engineering & Technology, vol. 16, No. 1, Jan./Feb. 1992, pp. 27–33.

Chandran, K. B., et al., Stress Distribution on the Cusps of a Polyurethane Trileaflet Heart Valve Prosthesis in the Closed Position, pp. 385–395.

Jansen, J, et al., New J–3 Flexible–Leaflet Polyurethane Heart Valve Prosthesis with Improved Hydrodynamic Performance, The International Journal of Artificial Organs, vol. 14, No. 10, 1991, pp. 655–660.

Yu, L. S., et al., Experimental Analysis of Mechanical Failure of Polyurethane Trileaflet Valve, 40th ACEMB, Sep. 10–12, 1987, p. 117.

Hilbert, S. L., et al., Evaluation of Explanted Polyurethane Trileaflet Cardiac Valve Prostheses, J. Thorac. Cardiovasc.Surg.1987, 94, pp. 419–429.

Wisman, C. B., et al., A Polyurethane Trileaflet Cardiac Valve Prosthesis: In Vitro and In Vivo Studies, Trans Am Soc Artif Intern Organs, 1982, vol. 28, pp. 164–168.

Mohri, H., et al., Design and Durability Test of Silastic Trileaflet Aortic Valve Prostheses, The Journal of Thoracic and Cardiovascular Surgery, vol. 65, No. 4, Apr. 1972, pp. 576–582.

Hufnagel, C. A., Reflections on the Development of Valvular Prostheses, Medical Instrumentation, vol. 11, No. 2, Mar.–Apr. 1977, pp. 74–76.

Roe, B. B. Late Follow–Up Studies on Flexible Leaflet Prosthetic Valves, Journal of Thoracic and Cardiovascular Surgery, vol. 58, No. 1, Jul., 1969, pp. 59–61.

Braunwald, N. S., et al., Complete Replacement of the Mitral Valve, J Thorac Cardiovasc Surg 1960, 40 pp 1–11.

Akutsu, T., et al., Polyurethane Artificial Heart Valves in Animals, pp. 1045–1048.

* cited by examiner

METHOD FOR MAKING POLYMER HEART VALVES WITH LEAFLETS HAVING UNCUT FREE EDGES

FIELD OF THE INVENTION

The present invention pertains to valves and in particular to tri-leaflet heart valve prostheses.

BACKGROUND OF THE INVENTION

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were substantially rigid and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular elastic valve body in which three flexible leaflets were mounted to a portion of the valve body, called a "stent," located at the circumference of the annulus. Some tri-leaflet valves used rigid leaflets. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue, or from a man-made material such as polyurethane or another biocompatible polymer.

Durability is a desirable characteristic of prosthetic heart valves, including tri-leaflet heart valves, because replacing such a valve is both expensive and dangerous for the patient. Another desirable characteristic of a prosthetic heart valve design is a reduction in thrombus accumulation on the valve.

SUMMARY OF THE INVENTION

The invention improves the durability of elastic heart valves by having molded, rather than cut, free edges. This removes the requirement to cut the free edge during the manufacturing process which reduces the likelihood that cracks will develop in the free edge and subsequently cause the valve to fail. Further, by removing the requirement to cut the free edge, the chance of thrombus accumulation on the valve is reduced.

In one aspect, the invention features a valve comprising an elastic valve body, a leaflet having an attachment edge and a free edge, the leaflet being coupled to the valve body on the attachment edge and the free edge of the leaflet having an uncut edge.

Implementations of the invention may include one or more of the following. The valve may further comprise a mold separation point on an inflow face of the leaflet away from the free edge. The free edge may have a full radius. The free edge may comprise a filleted edge.

In another aspect, the invention features an elastic valve body, a leaflet having an attachment edge and a free edge, the leaflet being coupled to the valve body on the attachment edge, and the free edge being molded.

Implementations of the invention may include one or more of the following. The mold separation point may be on an inflow face of the leaflet. The mold separation point may be on the free edge. The mold separation point may be on an outflow face of the leaflet. The leaflet may be molded in a partially open position. The leaflet may be molded in a fully open position.

In another aspect, the invention features a method of manufacturing a valve comprising forming an elastic valve body and a leaflet integral with the valve body, the leaflet having a free edge, the free edge having an uncut edge.

Implementations of the invention may include one or more of the following. Forming may comprise compression molding, injection molding or dip casting. The method may further comprise cutting an opening in the valve, the cutting occurring away from the free edge. Forming may comprise molding the leaflet in a partially open position. Forming may comprise molding the leaflet in a fully open position.

DESCRIPTION OF THE PREFERRED EMBODIMENTS

Figure 1:
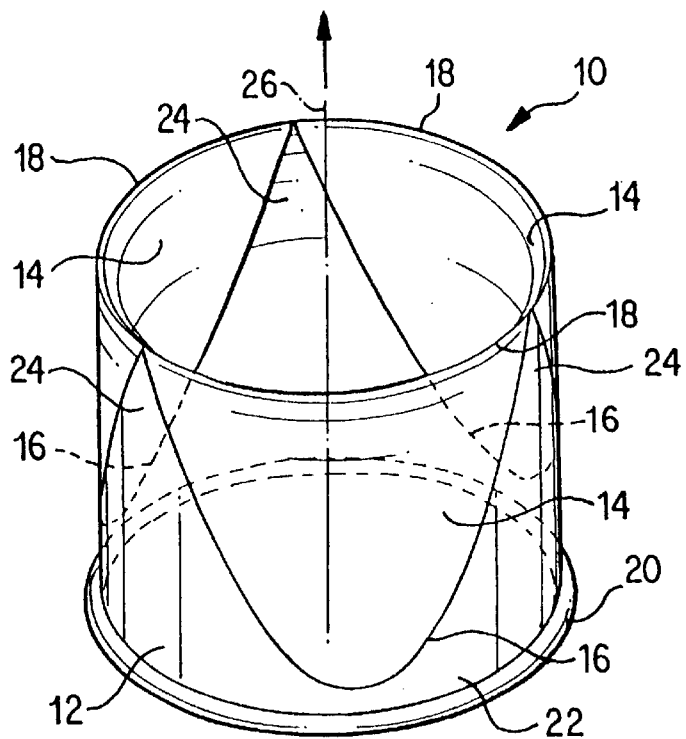
FIG. 1 is a perspective view of a polymer valve.

A tri-leaflet heart valve prosthesis 10 comprises an annular elastic valve body 12 and three flexible leaflets 14 made of a biocompatible polymer such as silicone or polyurethane, as shown in FIG. 1. Each leaflet has an attachment edge by which it is coupled to the valve body along an attachment curve 16. Each leaflet has a free edge 18 that is not coupled to the valve body. A sewing ring 20 is coupled to the base of the valve body 12 and provides a place for sutures to be applied when the valve is implanted. The valve body comprises an annular base 22 and a leaflet support, comprising three shaped posts 24, that support the leaflets 14.

Figure 2:
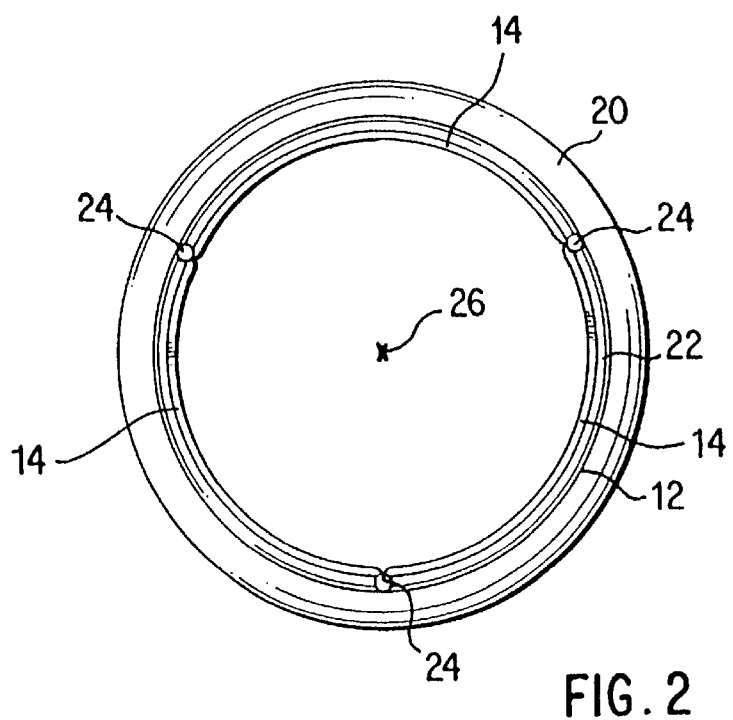
FIG. 2 is a top view of the polymer valve of FIG. 1.

When fluid flow is in the forward direction, i.e. in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIG. 2. With the leaflets in the open position shown in FIGS. 1 and 2, the valve presents little resistance to fluid flow.

Figure 3:
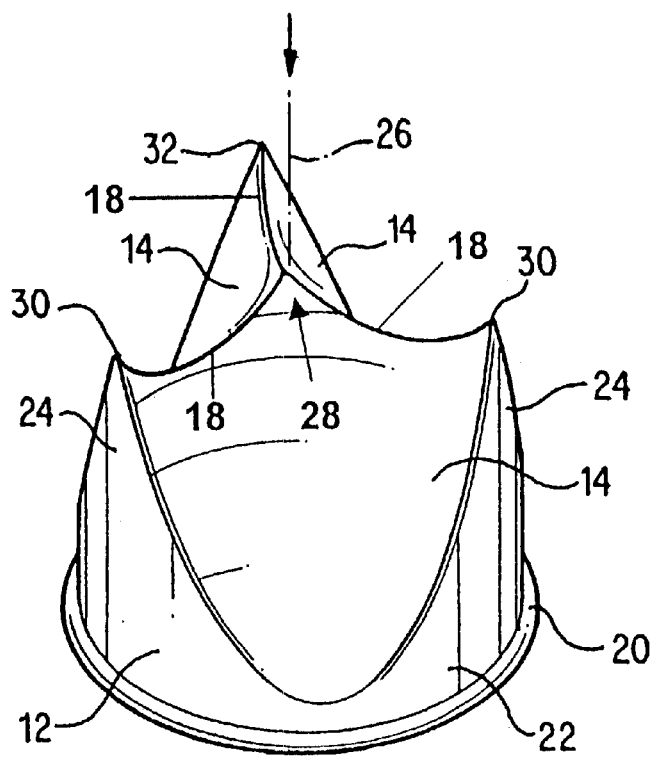
FIG. 3 is a perspective view of a polymer valve.
Figure 4:
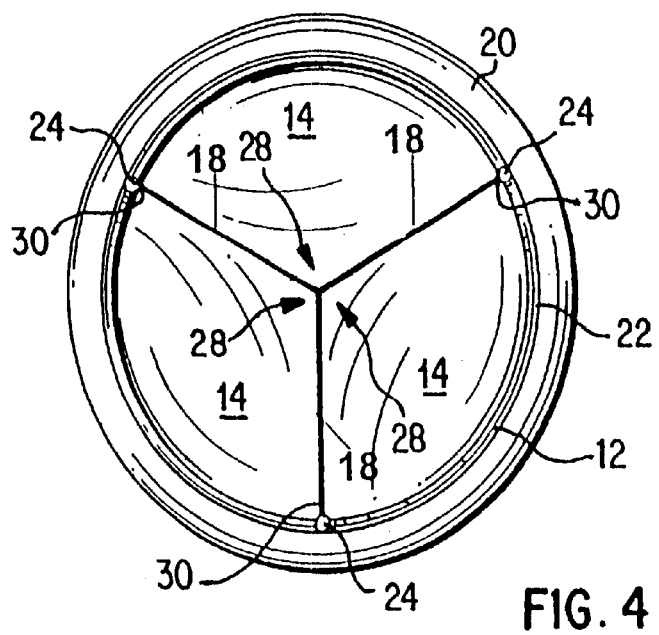
FIG. 4 is a top view of the polymer valve of FIG. 3.

When the pressure of blood flow is insufficient to overcome the elastic force biasing the valve toward a closed or partially closed position, the leaflets deflect toward axis 26, as shown in FIGS. 3 and 4. In this "closed" position, each leaflet would occlude more than one-third of the valve body's orifice were it not for the presence of the other leaflets. Consequently, when the three leaflets deflect toward axis 26, they engage each other and form coaptive areas along the free edges 18, which helps the valve seal against reverse flow. Further, when the leaflets press together, each leaflet forms a "triple point" 28 at the point where the three leaflets come together, as shown in FIGS. 3 and 4. The place where the leaflets 14 come together adjacent the posts 24 is called the "commissure" 30, as shown in FIGS. 3 and 4.

The first efforts at developing a heart valve for orthotopic implantation began in the early 1950s with single flap valves that were usually made from a cloth that was encapsulated by silicone rubber or polyurethane. These devices were implanted into animals and humans, without the benefit of invitro testing, by passing sutures or pins through the body of the valve and the heart tissue where they were joined. Such heart valves invariably failed from structural degradation. Often the failure point emanated from the sutures or pins used to attach the leaflets.

Figure 5:
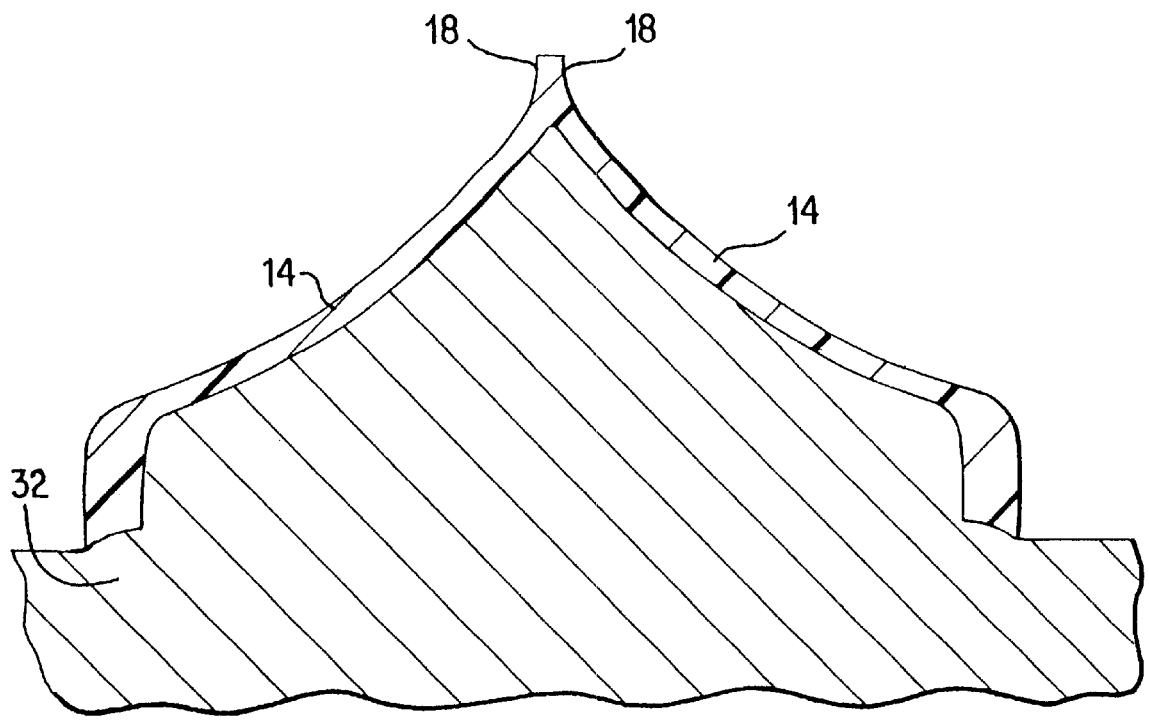
FIG. 5 is a section view of a prior art mold.
Figure 6:
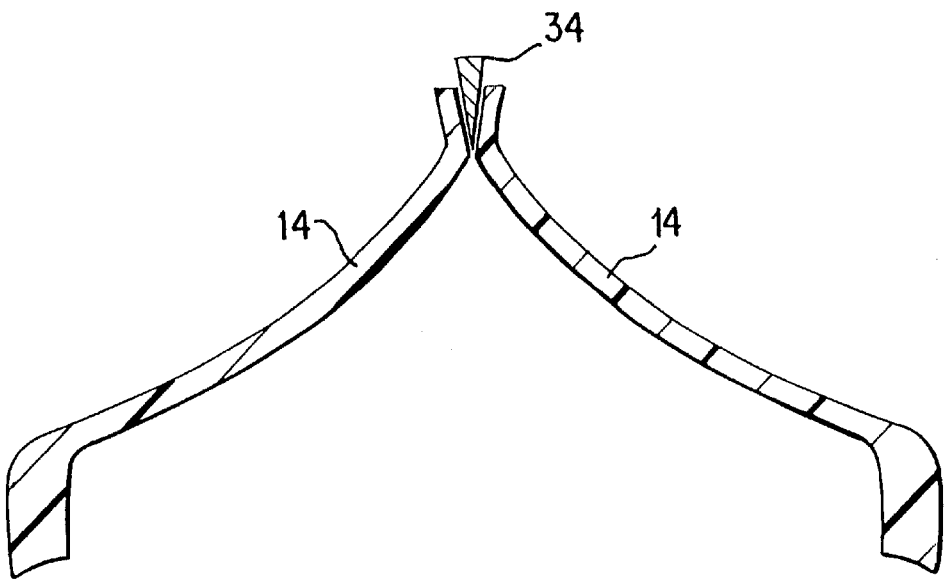
FIG. 6 is a section view of a prior art valve.

To avoid this mode of failure, complete valves were constructed so the sutures did not pass directly through the leaflets where they were bending with every cardiac cycle. Many of these complete valves were constructed by dip casting polyurethane or silicone on a dip casting mold that modeled the inflow surfaces of the valve. The inflow mold 32 was constructed so that the free edges 18 were molded together, as shown in FIG. 5. After the valve was separated from the mold, as shown in FIG. 6, the free edges of the valve were cut with a blade 34 to separate them. When these valves were taken to the point of structural failure, the failure typically emanated from the free edge 18 of the leaflet 14 where the leaflets 14 had been separated by the blade 34.

In another prior art approach to manufacturing tri-leaflet valves, the valves were compression molded of silicone with the metal stent fully encapsulated, but the leaflets were molded in the closed position and were cut apart to separate the free edges. In another prior art approach, silicone valves were compression molded without a stent with the leaflets molded in the closed position and then cut open. Valves manufactured using these two techniques suffered from structural failure with cracks emanating from the cut free edge.

In another prior art manufacturing technique, the valves were dip cast with the leaflets being in the partially open position. Again, however, the free edges of the leaflets were cut with a blade to separate them after molding.

Accelerated invitro testing and post mortem analysis of elastic valves constructed to allow opening and closing of the valve through elastic deformation have shown that failure emanates from the areas that combine high stresses, abrasive wear and cut edges. The free edges of such a valve encounter high stresses because of the movement and flexing associated with opening and closing as well as the stresses borne by the leaflets when fully open or fully closed. Further, as discussed above, in the prior art the free edges were separated by cutting the molded valve with a blade, leaving a rough and structurally damaged edge. These conditions increase the likelihood that the valve will fail at the free edges.

The invention comprises an elastic valve without cut edges or discontinuities in the structure of the valve in the areas of high stress. In particular, the invention is an elastic valve in which the free edges are molded rather than cut. Valves according to the invention will have improved durability because the sources of initial cracks have been removed from the design. In valves according to the invention, the rough areas that can promote the accumulation of thrombus are away from the flow separation areas.

Figure 7:
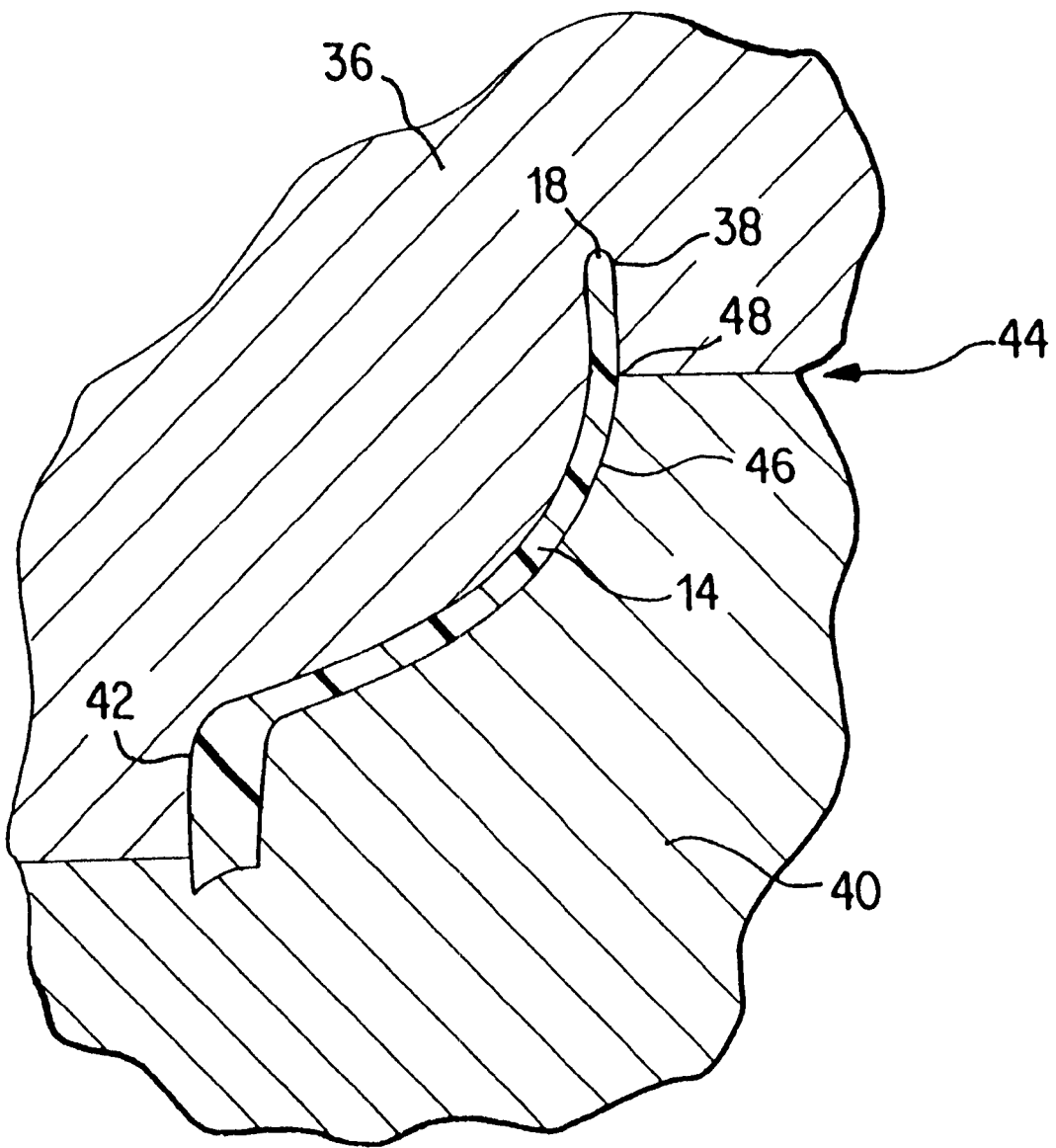
FIG. 7 is a section view of a mold according to the present invention.

An outflow mold 36, shown in FIG. 7, has a recess 38, which is designed in the shape of a leaflet free edge 18 and the portion of the leaflet 14 adjacent the free edge 18. An inflow mold 40 is shaped so that when it is mated with the outflow mold 36, as shown in FIG. 7, a recess 42 will form in the shape of a valve with a leaflet 14 in a partially closed position. Alternatively, the molds could be shaped so that the recess would be in the shape of a leaflet in a fully closed position.

A mold separation point 44 is preferably located on an inflow side 46 of the leaflet away from free edge 18. This is the preferred location because the mold separation point usually results in a discontinuity on the material surface, for example at point 48, which is better located on the inflow face of the valve where the velocity of blood is fairly high and the accumulation of thrombus is unlikely.

Figure 8:
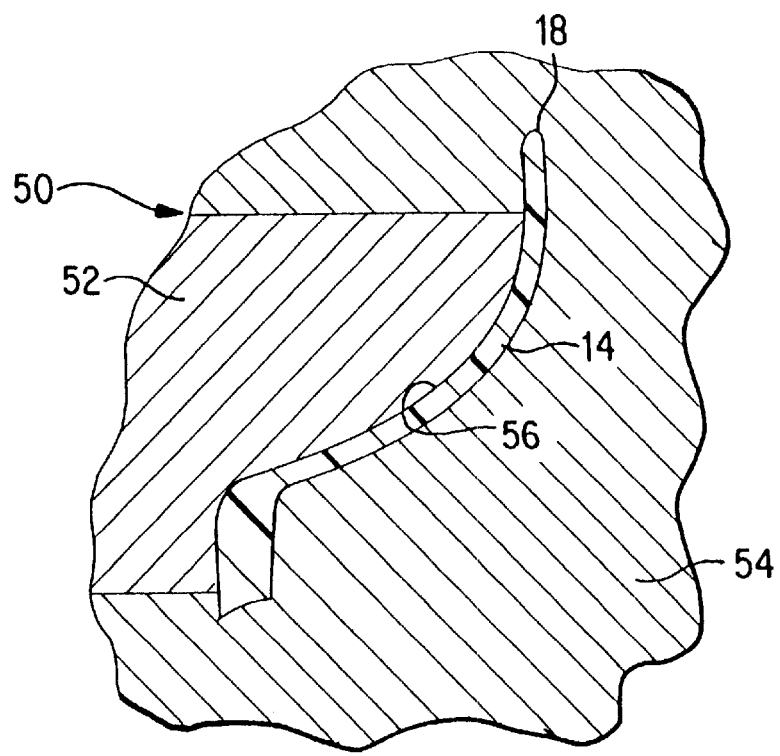
FIG. 8 is a section view of a mold according to the present invention.

Alternatively, a mold separation point 50 between outflow mold 52 and inflow mold 54 could be located on an outflow side 56 of the leaflet 14 away from free edge 18, as shown in FIG. 8.

Figure 9:
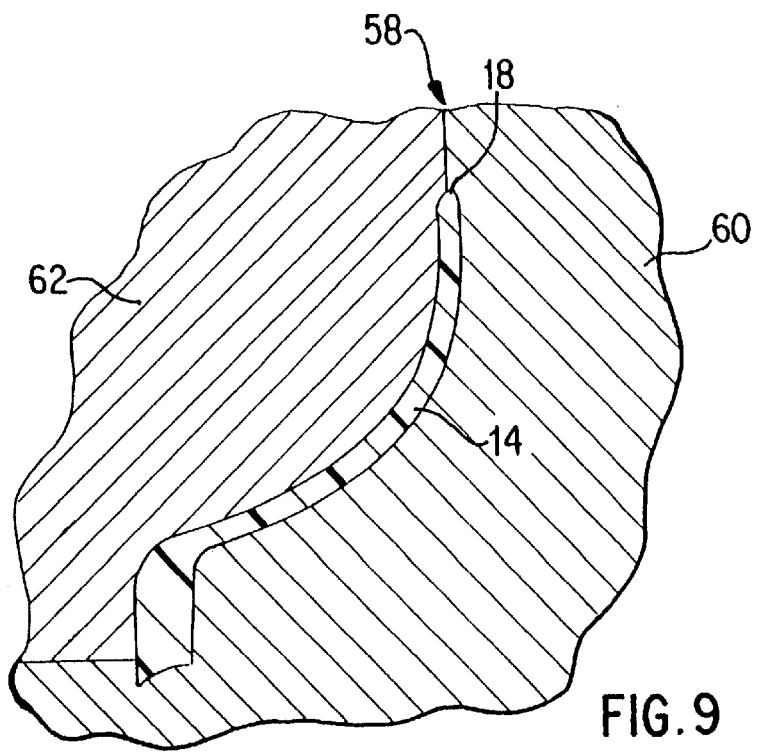
FIG. 9 is a section view of a mold according to the present invention.

Alternatively, a mold separation point 58 between an inflow mold 60 and an outflow mold 62 could be located on the free edge 18 of the leaflet, as shown in FIG. 9. A valve formed with such molds would have improved durability as compared to prior art valves.

Figure 10:
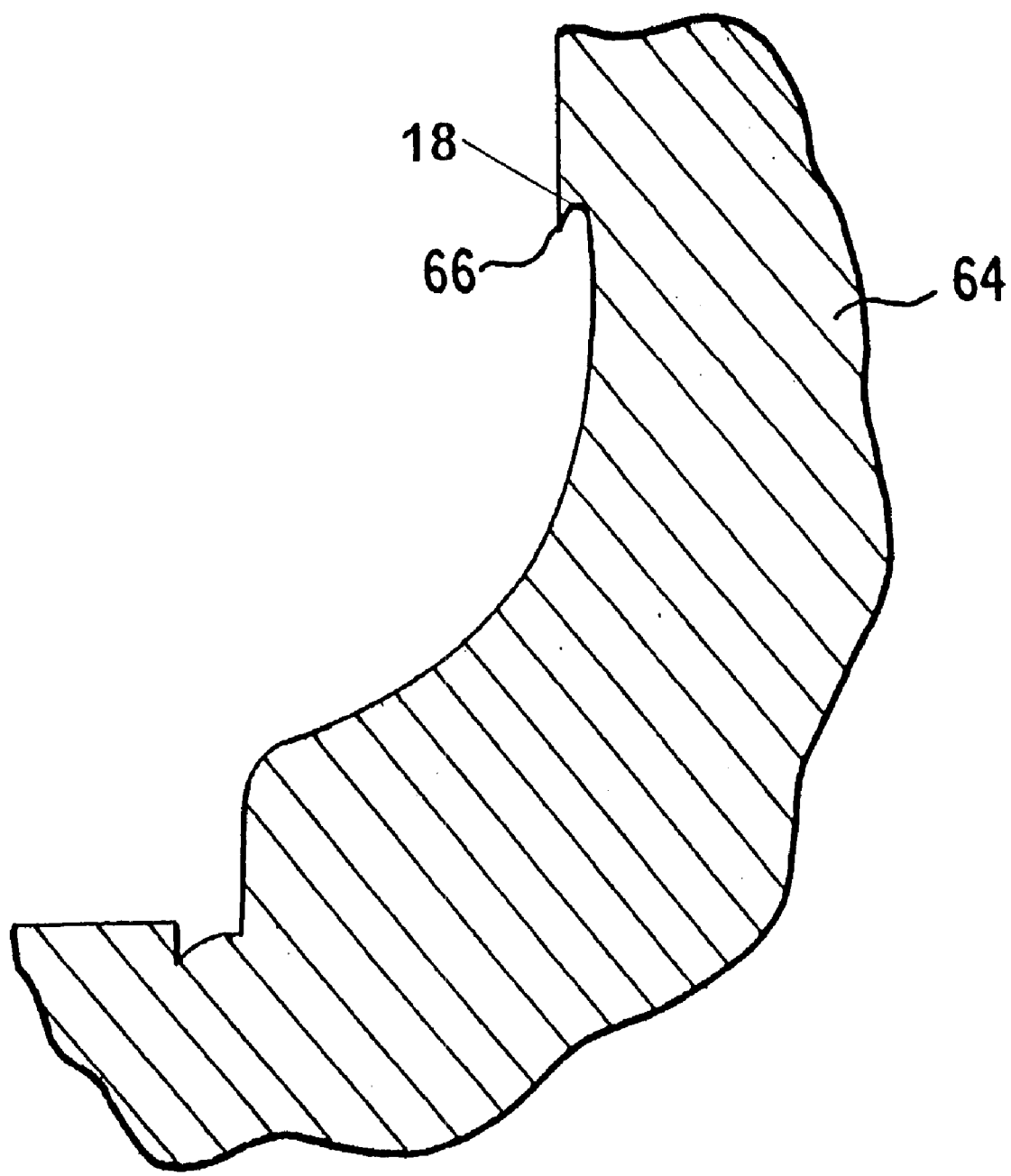
FIG. 10 is a section view of a mold according to the present invention.

The valve can be compression molded or injection molded using the molds illustrated in FIGS. 7, 8 and 9. An inflow mold 64, illustrated in FIG. 10, could also be dipped into polymer material to form a valve. A dip cast valve formed in such a manner would require trimming at point 66, but the cut would be away from the free edge 18 which would allow the free edge 18 to have a full radius and be less susceptible to failure than a valve with a cut free edge 18. Dip cast valves would have to be molded in the open position, as shown in FIG. 10, to allow the cut edge to be away from the molded edge.

Figure 11:
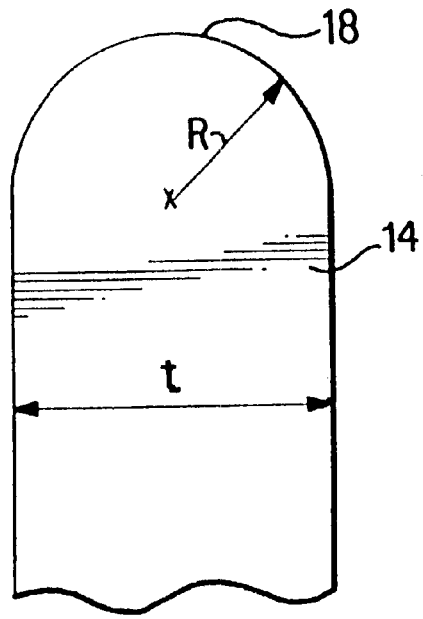
FIG. 11 is a section view of a leaflet according to the present invention.
Figure 12:
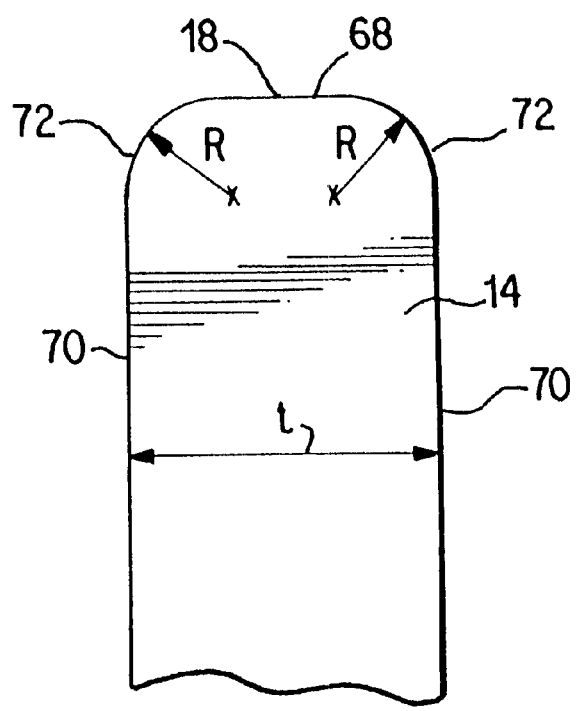
FIG. 12 is a section view of a leaflet according to the present invention.

The molded free edge 18 of a leaflet 14 can have a full radius $R=t/2$, where t is the thickness of the leaflet, as shown in FIG. 11. Preferably, the molded free edge 18 of the leaflet 14 will include a generally flat region 68 linked to the two faces 70 of the leaflet 14 by filleted edges 72. Each filleted edge has a radius $R<t/2$, where t is the thickness of the leaflet.

The foregoing describes preferred embodiments of the invention and is given by way of example only. The invention is not limited to any of the specific features described herein, but includes all variations thereof within the scope of the appended claims.

What is claimed is:

1. A method of manufacturing and implanting a prosthetic heart valve comprising:

1) providing a mold comprising a heart valve body portion and at least one leaflet portion integral with said valve body portion, said leaflet portion comprising a free edge portion;
2) forming a valve body having at least one polymeric leaflet in said mold, said leaflet comprising a free edge;
3) removing said valve body from said mold to obtain a heart valve having at least one leaflet with an uncut free edge; and
4) implanting said heart valve in a patient without cutting said free edge.

2. The method of claim 1 wherein said providing step comprises:
   providing an outflow mold having a recess in the shape of the free edge of said leaflet, said outflow mold defining a generally concave outflow side of said leaflet and at least a portion of a generally convex inflow side of said leaflet adjacent said free edge of said leaflet; and
   providing an inflow mold defining another portion of said inflow side of said leaflet, said outflow mold and said inflow mold meeting at a separation line on said inflow side of said leaflet.

3. The method of claim 1 wherein said providing step comprises:
   providing an inflow mold having a recess in the shape of the free edge of said leaflet, said inflow mold defining a generally convex inflow side of said leaflet and at least a portion of a generally concave outflow side of said leaflet adjacent said free edge of said leaflet; and
   providing an outflow mold defining another portion of said outflow side of said leaflet, said inflow mold and said outflow mold meeting at a separation line on said outflow side of said leaflet.

4. The method of claim 1 wherein said providing step comprises:
   providing an outflow mold defining a generally concave outflow side of said leaflet; and
   providing an inflow mold defining a generally convex inflow side of said leaflet, said outflow mold and said inflow mold meeting at a separation line on said free edge of said leaflet.

5. The method of claim 1 wherein said providing step comprises:
   providing an inflow mold having a recess in the shape of the free edge of said leaflet, said inflow mold defining a generally convex inflow side of said leaflet and at least a portion of an outflow side of said leaflet adjacent said free edge of said leaflet, and said inflow mold terminating at a point spaced away from said free edge, said point forming a line along said outflow side of said leaflet;
and wherein said method further comprises trimming said leaflet along said line.

6. The method of claim 1 wherein said forming step comprises dip casting.

7. The method of claim 1, wherein said forming step comprises compression molding.

8. The method of claim 1 wherein said forming step comprises injection molding.

9. The method of claim 1 wherein said removing step further comprises the step of cutting an opening in the valve, said cutting occurring away from said free edge.

10. The method of claim 1 wherein said forming step comprises molding the leaflet in a partially open position.

11. The method of claim 1 wherein said forming step comprises molding the leaflet in a fully open position.

12. A method of making and implanting a prosthetic heart valve comprising:
   providing a mold for a heart valve having a valve body and a plurality of polymeric leaflets, each of said leaflets comprising a free edge, said mold comprising a free edge portion for forming each said free edge independently of the other free edges;
   forming said valve body and said plurality of leaflets in said mold;
   removing said valve body and said leaflets from said mold without cutting any of said free edges; and
   implanting said heart valve in a patient.

* * * * *